(12) United States Patent
Goud et al.

(10) Patent No.: US 7,488,809 B2
(45) Date of Patent: Feb. 10, 2009

(54) CHIMERIC POLYPEPTIDE COMPRISING THE FRAGMENT B OF SHIGA TOXIN AND PEPTIDES OF THERAPEUTIC INTEREST

(75) Inventors: Bruno Goud, Paris (FR); Ludger Johannes, Paris (FR)

(73) Assignees: Insem-Transfert, Paris (FR); Universite Pierre Et Marie Curie (UPMC), Paris (FR)

( * ) Notice: Subject to any disclaimer, the term of this patent is extended or adjusted under 35 U.S.C. 154(b) by 0 days.

(21) Appl. No.: 10/443,614

(22) Filed: May 21, 2003

(65) Prior Publication Data

US 2004/0047883 A1  Mar. 11, 2004

Related U.S. Application Data

(63) Continuation of application No. 09/484,471, filed on Jan. 18, 2000, now Pat. No. 6,613,882, which is a continuation of application No. PCT/FR98/01573, filed on Jul. 17, 1998.

(30) Foreign Application Priority Data

Jul. 18, 1997 (FR) .................................. 97 09185

(51) Int. Cl.
*C07K 14/25* (2006.01)
(52) U.S. Cl. .................... 530/402; 530/300; 536/23.1
(58) Field of Classification Search ............. 512/2; 514/44
See application file for complete search history.

(56) References Cited

U.S. PATENT DOCUMENTS

| | | | | |
|---|---|---|---|---|
| 5,198,344 | A | 3/1993 | Croop et al. | 435/69.1 |
| 5,338,839 | A | 8/1994 | McKay et al. | 536/235 |
| 5,350,890 | A | 9/1994 | Fairbrother et al. | 200/5 |
| 5,747,028 | A | 5/1998 | Calderwood et al. | 424/93.2 |
| 5,763,165 | A | 6/1998 | Boon-Falleur et al. | 435/6 |
| 5,980,898 | A | 11/1999 | Glenn et al. | 424/184.1 |
| 6,197,299 | B1 | 3/2001 | Dohlsten | 424/183.1 |
| 6,482,586 | B1 | 11/2002 | Arab et al. | 435/4 |

FOREIGN PATENT DOCUMENTS

| | | |
|---|---|---|
| EP | 130132 A1 | 1/1985 |
| EP | 439 954 | 8/1991 |
| EP | 532090 A2 | 3/1993 |
| EP | 739984 A1 | 10/1996 |
| WO | WO 91/09871 A1 | 7/1991 |
| WO | WO 93/16186 | 8/1993 |
| WO | WO 93/17115 | 9/1993 |
| WO | WO 95/14085 A2 | 5/1995 |
| WO | WO 95/14085 A3 | 5/1995 |
| WO | WO 96/16178 A1 | 5/1996 |
| WO | WO 97/13410 | 4/1997 |
| WO | WO 98/11229 A2 | 3/1998 |
| WO | WO 99/59627 A2 | 11/1999 |
| WO | WO 99/59627 A3 | 11/1999 |

OTHER PUBLICATIONS

Definition of "specific" on Merriam-Wester Online downloaded on Aug. 2, 2005.*
Rimoldi et al., Int J Cancer. Sep. 9, 1999;82(6):901-7.*
Chang et al., Gynecol Oncol. May 2005;97(2):342-7.*
Cohen et al., The Journal of Immunology, 2003, 170: 4349-4361.*
Fominaya et al., J. Biol. Chem., 1996, vol. 271, pp. 10560-10568.*
Allinquant et al. "Downregulation of Amyloid Precursor Protein Inhibits Neurite Outgrowth In Vitro." *J. Cell Biol.* 1995;128(5):919-27.
Austyn. "New insights into the mobilization and phagocytic activity of dendritic cells." *J Exp Med.* Apr. 1, 1996;183(4):1287-92.
Boël et al. "*BAGE*: a New Gene Encoding an Antigen Recognized on Human Melanomas by Cytolytic T Lymphocytes." *Immunite* 1995;2:167-75.
Boon "Toward a genetic analysis of tumor rejection antigens." *Adv Cancer Res*. 1992;58:177-210.
Bos "The skin as an organ of immunity." *Clin Exp Immunol.* Jan. 1997;107 Suppl 1:3-5.
Bower et al. "Cloning and Characterization of the *Bacillus subtilis birA* Gene Encoding a Repressor of the Biotin Operon." *J. Bacteriology* 1995;177(9):2572-75.
Brichard et al. "The Tyrosinase Gene Codes for an Antigen Recognized by Autologous Cytolytic T Lymphocytes on HLA-A2 Melanomas." *J. Exp. Med.* 1993;178:489-95.
Calderwood et al. "Nucleotide sequence of the Shiga-like toxin genes of *Escherichia coli.*" *Proc. Natl. Acad. Sci. USA* 1987;84(13):4364-68.
Cella et al. "Origin, maturation and antigen presenting function of dendritic cells." *Curr Opin Immunol*. Feb. 1997;9(1):10-6.
Chicz et al. "Analysis of MHC-presented peptides: applications in autoimmunity and vaccine development." *Immunol. Today* 1994;15(4):155-60.
Ciernik et al. "Mutant Oncopeptide Immunization Induces CTL Specifically Lysing Tumor Cells Endogenously Expressing the Corresponding Intact Mutant p53." *Hybridoma* 1995;14:139-42.
Coulie et al. "A New Gene Coding for a Differentiation Antigen Recognized by Autologous Cytolytic T Lymphocytes on HLA-A2 Melanomas." *J. Exp. Med.* 1994;180:35-42.
Curti "Physical barriers to drug delivery in tumors." *Crit Rev Oncol Hematol*. Feb. 1993;14(1):29-39.

(Continued)

*Primary Examiner*—Misook Yu
(74) *Attorney, Agent, or Firm*—Venable LLP; Michael A. Gollin; Nancy J. Axelrod

(57) ABSTRACT

The invention pertains to methods for using chimeric polypeptides of the formula:

Figure 1B:
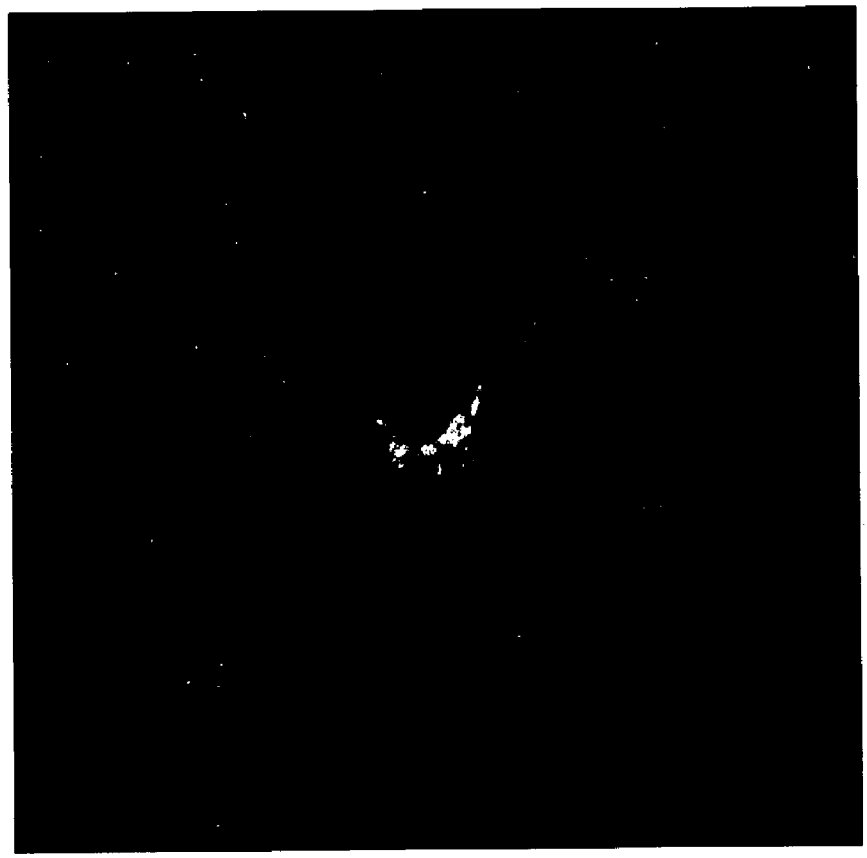

B—X wherein B represents the B fragment of Shiga toxin or a functional equivalent thereof, and X represents one or more polypeptides of therapeutic significance. Compositions for therapeutic use comprising the polypeptide B—X are also included.

8 Claims, 5 Drawing Sheets

OTHER PUBLICATIONS

Davis et al. "DNA-Mediated Immunization in Mice Induces a Potent MHC Class I-Restricted Cyto-toxic T Lymphocyte Response to the Hepatitis B Envelope Protein." *Hum. Gene Therapy* 1995;6:1447-56.

De Plaen et al. "Structure, chromosomal localization, and expression of 12 genes of the *MAGE* family." *Immunogenetics* 1994;40:360-69.

Edelman "Vaccine adjuvants." *Rev Infect Dis.* May-Jun. 1980;2(3):370-83.

Ezzell "Cancer 'vaccines': An idea whose time has come?" *J. NIH Res.* 1995;7:46-9.

Feltkamp et al. "Cytotoxic T lymphocytes raised against a subdominant epitope offered as a synthetic peptide eradicate human papillomavirus type 16-induced tumors." *Eur J Immunol.* Sep. 1995;25(9):2638-42.

Feltkamp et al. "Vaccination with cytotoxic T lymphocyte epitope-containing peptide protects against a tumor induced by human papillomavirus type 16-transformed cells." *Eur. J. Immunol.* 1993;23:2242-9.

Flørenes et al. "Expression of the neuroectodermal intermediate filament nestin in human melanomas." *Cancer Res.* Jan. 15, 1994;54(2):354-6.

Furukawa et al. "Clonal Expansion of CD8+Cytotoxic T Lymphocytes against Human T Cell Lymphotrophic Virus Type I (HTLV-I) Genome Products in HTLV-I-associated Myelopathy/Tropical Spastic Paraparesis Patients." *J. Clin. Invest.* 1994;94:1830-39.

Gao et al. "Recombinant *Salmonella typhimurium* strains that invade nonphagocytic cells are resistant to recognition by antigen-specific cytotoxic T lymphocytes." *Infect Immun.* Sep. 1992;60(9):3780-9.

Glenn et al. "Skin immunization made possible by cholera toxin." *Nature.* Feb. 26, 1998;391(6670):851.

Gnjatic et al. "Mapping and ranking of potential cytotoxic T epitopes in the p53 protein: effect of mutations and polymorphism on peptide binding to purified and refolded HLA molecules." *Eur. J. Immunol.* 1995;25:1638-42.

Gura "Systems for identifying new drugs are often faulty." *Science.* Nov. 7, 1997;278(5340):1041-2.

Hartwell et al. "Integrating genetic approaches into the discovery of anticancer drugs." *Science.* Nov. 7, 1997;278(5340):1064-8.

Head et al. "Preparation of VT1 and VT2 hybrid toxins from their purified dissociated subunits. Evidence for B subunit modulation of a subunit function." *J Biol Chem.* 1991;266(6):3617-21.

Heemels et al. "Generation, translocation, and presentation of MHC class I-restricted peptides." *Annu Rev Biochem.* 1995;64:463-91.

Huang et al. "Role of bone marrow-derived cells in presenting MHC class I-restricted tumor antigens." *Science.* May 13, 1994;264(5161):961-5.

Hui et al. "An isoform of the Golgi t-SNARE, syntaxin 5, with an endoplasmic reticulum retrieval signal." *Mol Biol Cell.* Sep. 1997;8(9):1777-87.

Jain "Barriers to drug delivery in solid tumors." *Sci Am.* Jul. 1994;271(1):58-65.

Johannes et al. "Retrograde Transport of KDEL-bearing B-fragment of Shiga Toxin." *J. of Biological Chemistry* 1997;272(31):19554-19561.

Johannes et al. "Shiga toxin as a tool to study retrograde transport." *Molecular Biology of the Cell* 1996;7(Supp.):75a (Annual Meeting of the 6th International Congress of Cell Biology and the 36th American Society for Cell Biology, San Francisco, California).

Kavanaugh et al. "Immunologic dysfunction in cancer." *Hematol Oncol Clin North Am.* Aug. 1996;10(4):927-51.

Kawakami et al. "Identification of the Immunodominant Peptides of the MART-1 Human Melanoma Antigen Recognized by the Majority of HLA-A2-restricted Tumor Infiltrating Lymphocytes." *J. Exp. Med.* 1994;180:347-52.

Ke et al. "Ovalbumin injected with complete Freund's adjuvant stimulates cytolytic responses." *Eur J Immunol.* Feb. 1995;25(2):549-53.

Kim et al. "Dynamic Measurement of the pH of the Golgi Complex in Living Cells Using Retrograde Transport of the Verotoxin Receptor." *J. Cell Biol.* 1996;134(6):1387-99.

Kimmel et al. "In vitro drug sensitivity testing in human gliomas." *J Neurosurg.* Feb. 1987;66(2):161-71.

Kovacsovics-Bankowski et al. "Efficient major histocompatibility complex class I presentation of exogenous antigen upon phagocytosis by macrophages." *Proc Natl Acad Sci U S A.* Jun. 1, 1993;90(11):4942-6.

Kurts et al. "Constitutive class I-restricted exogenous presentation of self antigens in vivo." *J Exp Med.* Sep. 1, 1996;184(3):923-30.

Lamb "Nucleotide sequence of cloned cDN coding for preproricin." *Eur. J. of Biochem.* 1995;148(2):265-70.

Lee et al. "Major histocompatibility complex class I presentation of exogenous soluble tumor antigen fused to the B-fragment of Shiga toxin." *Eur. J. Immunol.* 1998;28:2726-2737.

Lewis et al. "A human homologue of the yeast HDEL receptor." *Nature* 1990;348:162-63.

Lewis et al. "Ligand-Induced Redistribution of a Human KDEL Receptor from the Golgi Complex to the Endoplasmic Reticulum." *Cell* 1992;68:353-64.

Lingwood et al. "erotoxins and Their Glycolipid Recetpros." *Adv. Lipid Res.* 1993;25:189-211.

Lipford et al. "CpG-containing synthetic oligonucleotides promote B and cytotoxic T cell responses to protein antigen: a new class of vaccine adjuvants." *Eur J Immunol.* Sep. 1997;27(9):2340-4.

Matousek et al. "Distinct effects of recombinant cholera toxin B subunit and holotoxin on different stages of class II MHC antigen processing and presentation by macrophages." *J Immunol.* Jun. 1, 1996;156(11):4137-45.

Monaco "A molecular model of MHC class-I-restricted antigen processing." *Immunol Today.* May 1992;13(5):173-9.

Moore et al. "Introduction of soluble protein into the class I pathway of antigen processing and presentation." *Cell.* Sep. 9, 1988;54(6):777-85.

Murray et al. "Identification of Target Antigens for the Human Cytotoxic T Cell Response to Epstein-Barr Virus (EBV): Implications for the Immune Control of EBV-positive Malignancies." *J. Exp. Med.* 1992;176:157-68.

Nair et al. "Soluble proteins delivered to dendritic cells via pH-sensitive liposomes induce primary cytotoxic T lymphocyte responses in vitro." *J Exp Med.* Feb. 1, 1992;175(2):609-12.

Nestle et al. "Vaccination of melanoma patients with peptide- or tumor lysate-pulsed dendritic cells." *Nat Med.* Mar. 1998;4(3):328-32.

O'Brien et al. "Shiga Toxin: Biochemistry, Genetics, Mode of Action, and Role in Pathogenesis." *Curr. Top. Microbiol. Immunol.* 1992;180:65-94.

Pan et al. "Regression of established tumors in mice mediated by the oral administration of a recombinant *Listeria monocytogenes* vaccine." *Cancer Res.* Nov. 1, 1995;55(21):4776-9.

Peace et al. "Induction of T Cells Specific for the Mutated Segment of Oncogenic P21-*ras* protein by Immunization In Vivo with the Oncogenic Protein." *J. Immunother* 1993;14:110-4.

Pelham et al. "Toxin entry: how reversible is the secretory pathway?" *Trends Cell Biol.* 1992;2:183-85.

Perez et al. "Antennapedia homeobox as a signal for the cellular internalization and nuclear addressing of a small exogenous peptide." *J Cell Sci.* Aug. 1992;102 ( Pt 4):717-22.

Pieters "MHC class II restricted antigen presentation." *Curr Opin Immunol.* Feb. 1997;9(1):89-96.

Pudymaitis et al. "Susceptibility to verotoxin as a function of the cell cycle." *J Cell Physiol.* Mar. 1992;150(3):632-9.

Rapak et al. "Retrograde transport of mutant ricin to the endoplasmic reticulum with subsequent translocation to the cytosol." *Proc. Natl. Acad. Sci. USA* 1997;94:3783-3788.

Rehermann et al. "The Cytotoxic T Lymphocyte Response to Multiple Hepatitis B Virus Polymerase Epitopes During and After Acute Viral Hepatitis." *J. Exp. Med.* 1995;181:1047-58.

Reis e Sousa et al. "Major histocompatibility complex class I presentation of peptides derived from soluble exogenous antigen by a subset of cells engaged in phagocytosis." *J Exp Med.* Sep. 1, 1995;182(3):841-51.

Redfield et al. "Disseminated vaccinia in a military recruit with human immunodeficiency virus (HIV) disease." *N Engl J Med.* Mar. 12, 1987;316(11):673-6.

Rock "A new foreign policy: MHC class I molecules monitor the outside world." *Immunol Today.* Mar. 1996;17(3):131-7.

Rosenberg et al. "Treatment of patients with metastatic melanoma with autologous tumor-infiltrating lymphocytes and interleukin 2." *J Natl Cancer Inst.* Aug. 3, 1994;85(15):1159-66.

Sabzevari et al. "Human cytotoxic T-cells suppress the growth of spontaneous melanoma metastases in SCID/hu mice." *Cancer Res.* Oct. 15, 1993;53(20):4933-7.

Sallusto et al. "Efficient presentation of soluble antigen by cultured human dendritic cells is maintained by granulocyte/macrophage colony-stimulating factor plus interleukin 4 and downregulated by tumor necrosis factor α." *J Exp Med.* Apr. 1, 1994;179(4):1109-18.

Sandvig et al. "Endocytosis, intracellular transport, and cytotoxic action of Shiga toxin and ricin." *Physiol Rev.* Oct. 1996;76(4):949-66.

Sandvig et al. "Retrograde Transport from the Golgi complex to the ER of Both Shiga Toxin and the Nontoxic Shiga B-gragment Is Regulated by Butryric Acid and Camp." *J. Cell. Biol.* 1994;126(1):53-64.

Sandvig et al. "Retrograde transport of endocytosed Shiga toxin to the endolasmic reticulum." *Nature* 1992;358:510-12.

Schutze-Redelmeier et al. "Introduction of exogenous antigens into the MHC class I processing and presentation pathway by *Drosophila* antennapedia homeodomain primes cytotoxic T cells in vivo." *J Immunol.* Jul. 15, 1996;157(2):650-5.

Seidah et al. "Complete Amino Acid Sequence of *Shigella* Toxin B-chain." *J. Biol. Chem.* 1986;261(30):13928-31.

Smigel "Women flock to ABMT for breast cancer without final proof." *J Natl Cancer Inst.* Jul. 5, 1995;87(13):952-5.

Snider "The mucosal adjuvant activities of ADP-ribosylating bacterial enterotoxins." *Crit Rev Immunol.* 1995;15(3-4):317-48.

Spitler et al. "Cancer vaccines: the interferon analogy." *Cancer Biother.* 1995 Spring;10(1):1-3.

Steinman "The dendritic cell system and its role in immunogenicity." *Annu Rev Immunol.* 1991;9:271-96.

Stevenson et al. "Protection against influenza virus encephalitis by adoptive lymphocyte transfer." *Virology.* May 26, 1997;232(1):158-66.

Strockbine et al. "Cloning and Sequencing of the Genes for Shiga Toxin from *Shigella dysenteriae* Type 1." *J. Bacteriology* 1988;170(3):1116-22.

Su et al. "Construction of Stable LamB-Shiga Toxin B Subunit Hybrids: Analysis of Expression in *Salmonella typhimurium aroA* Strains and Stimulation of B Subunit-Specific Mucosal and Serum Antibody Responses." *Infection and Immunity* 1992;60:3345-59.

Traversari et al. "A Nonapeptide Encoded by Human Gene MAGE-1 Is Recognized on HLA-A1 by Cytolytic T Lymphocytes Directed against Tumor Antigen MZ2-E." *J. Exp. Med.* 1992;176:1453-57.

Traversari et al. "Transfection and expression of a gene coding for a human melanoma antigen recognized by autologous cytolytic T lymphocytes." *Immunogenetics.* 1992;35(3):145-52.

Tsao et al. "A versatile plasmid expression vector for the production of biotinylated proteins by site-specific, enzymatic modification in *Escherichia coli*." *Gene* 1996;169:59-64.

van der Bruggen et al. "A gene encoding an antigen recognized by cytolytic T lymphocytes on a human melanoma." *Science.* Dec. 13, 1991;254(5038):1643-7.

van der Bruggen et al. "A peptide encoded by human gene MAGE-3 and presented by HLA-A2 induces cytolytic T lymphocytes that recognize tumor cells expressing MAGE-3." *Eur J Immunol.* Dec. 1994;24(12):3038-43.

Van den Eynde et al. "A New Family of Genes Coding for an Antigen Recognized by Autologous Cytoloic T Lymphocutes on a Human Melanoma." *J. Exp. Med.* 1995;182:689-98.

Watts "Capture and processing of exogenous antigens for presentation on MHC molecules." *Annu Rev Immunol.* 1997;15:821-50.

Wu et al. "Induction of mucosal immunity by intranasal application of a streptococcal surface protein antigen with the cholera toxin B subunit." *Infect Immun.* Jan. 1993;61(1):314-22.

Denning, Gerene M. et al., "Processing of mutant cystic fibrosis transmembrane conductace regulator is temperature-sensitive," *Nature*, vol. 358:761-764 (1992).

Imai, Yasuhisa et al., "Sequence analysis of the *MAGE* gene family encoding human tumor-rejection antigens," *Gene*, vol. 160:287-290 (1995).

Maloney, M. et al., "Interaction of Verotoxins with Glycosphingolipids," *Trends in Glycoscience and Glycotechnology*, vol. 5(21):23-31 (1993).

* cited by examiner

CHIMERIC POLYPEPTIDE COMPRISING THE FRAGMENT B OF SHIGA TOXIN AND PEPTIDES OF THERAPEUTIC INTEREST

This application is a divisional of U.S. patent application Ser. No. 09/484,471, issuing, filed on Jan. 18, 2000, which is a continuation of PCT/FR98/01578, filed on Jul. 17, 1998, which claims priority to French Patent Application Serial No. 9709185, filed on Jul. 18, 1997. The entire contents of each of the aforementioned patent applications are hereby incorporated herein by reference.

The invention relates to means and to their use for intracellular transport of proteins or polypeptides, also to the membrane presentation of certain epitopes.

Retrograde transport can be defined as the movement of molecules from the cell membrane to the endoplasmic reticulum (ER), passing if necessary via the Golgi apparatus. This mechanism has been demonstrated for certain classes of proteins of the endoplasmic reticulum carrying the tetrapeptide KDEL at the carboxy terminal (or HDEL in starch). A great deal of biochemical and morphological evidence indicates that those proteins leave the endoplasmic reticulum, reach the Golgi apparatus in which modifications are made to their carbohydrate chain and are then redirected to the endoplasmic reticulum. The tetrapeptide KDEL is a retention signal which traps the peptide or protein to which it is attached in the endoplasmic reticulum, such trapping taking place by interaction at a receptor protein for the KDEL motif described by Lewis M. J. et al in Nature, 348 (6297):162: 3, 1990, 8 Nov.

Other evidence for the existence of intracellular retrograde transport arises from a study of certain bacterial toxins which enter the cytosol of eukaryotic cells after passing into the endoplasmic reticulum (Pelham et al (1992) Trends cell. Biol., 2: 183-185). A particular example which has been studied is that of the Shiga toxin from Shigella dysenteriae, also *E. coli* Shiga-like toxins. Such toxins are composed of two polypeptide chains; one (the A fragment) is the toxic fragment and carries a deadenylase activity which inhibits protein synthesis by acting on the 28S ribosomal RNA, while the other sub-unit (the B fragment) enables the toxin to bind to the target (O'Brien et al (1992), Curr. Top. Microbiol. Immunol. 180: 65-94). Electron microscope studies have shown that Shiga toxin can be detected in the ER of A431, Vero, and Daudi cells in particular (Sandvig et al, 1992 and 1994; KHINE, 1994). Further, treating cells with a fungal metabolite which cause the loss of the Golgi apparatus structure (brefeldin A) protects the cells against Shiga toxin thus suggesting that they traverse the Golgi apparatus before reaching the ER. Finally, Kim et al (1996) have confirmed that the B fragment of the toxin is localised in the Golgi apparatus.

The following references demonstrate the state of the art as regards retrograde transport, in particular transport of the B fragment of Shiga toxin in the ER: Sandvig et al (1992), Nature 358:510-512; Sandvig et al (1994) J. Cell. Biol 126: 53-64; Kim et al (1996) J. Cell. Biol 134: 1387-1399.

Intracellular transport is defined as the ensemble of exchanges between the different cellular compartments.

The authors of the present application have observed that the B fragment is not only moved towards the ER, but also to the nucleus of hematopoietic lines, in particular dendritic cells and macrophages.

The authors have shown that those cells, incubated in the presence of two micromoles of B-Gly-KDEL fragment, as described below, for 3 hours then fixed, have a reactivity with specific antibodies against the toxin in the nucleus and even in the nucleole of such cells (unpublished results) which clearly indicate the existence of intracellular transport of that fragment.

The present invention results from observations on intracellular transport of the B fragment of Shiga toxin (B fragment) and uses its routing properties to construct a chimeric polypeptide sequence containing:

either a peptide or a polypeptide of therapeutic significance bound to said fragment or any functional equivalent thereof;

or a polynucleotide sequence carrying a sequence the expression of which is desired. The B fragment and the polynucleotide sequence are coupled using any technique which is known to the skilled person and in particular that described by Allinquant B. et al in the Journal of Cell Biology 1288 (5): 919-27 (1995).

In addition to covalent coupling of DNA molecules or other molecules to the B fragment, coupling can be via a strong non covalent interaction. To this end and by way of example, the cDNA of the B fragment is fused with that of streptavidin or with any other avidin derivative using known methods (Johannes et al (1987), J. Biol. Chem., 272: 19554-19561).

The protein resulting from fusion (B-streptavidin) can react with biotinylated DNA obtained by PCR using biotinylated primers, or with any other biotinylated substance. The resulting complex is bound to target cells and should be transported like the intracellular B fragment.

A further coupling method employs site-specific biotinylation of the B fragment. To this end, the cDNA of the B fragment is fused with cDNA coding for the BirA enzyme recognition site (Boer et al (1995), J. Bacterial, 177: 2572-2575; Saou et al (1996) Gene, 169: 59-64). After in vitro biotinylation, the B fragment is bound to other biotinylated molecules (such as cDNA, see above) via streptavidin or any other tetravalent avidine derivative.

The term "functional equivalent" means any sequence derived from the B fragment by mutation, deletion or addition, and with the same routing properties as the B fragment.

More precisely, a functional equivalent can be constituted by any fragment with the same retrograde transport properties and even intracellular transport to the nucleus as those described for the B fragment. Examples which can be cited are the B fragment of verotoxin described in the Proceedings of the National Academy of Sciences of the United States of America, 84 (13): 4364-8 1987, July, or the B fragment from ricin described by Lamb F. I. Et al in the European Journal of Biochemistry, 148(2): 265-70 (1995). After describing the particular transport properties of such fragments, the skilled person will be able to select the fragment which would be the best candidate as a vector for routing any sequence in any cellular compartment.

Figure 1A:

Thus the present invention encompasses the use of the B fragment of Shiga toxin or any other sub unit of bacterial toxins which would have comparable activities, in particular routing properties analogous to those of fragment B, including polypeptides miming the Shiga toxin B fragment. These polypeptides, and in general these functional equivalents, can be identified by screening methods which have in common the principle of detecting the interaction between random peptide sequences and the $Gb_3$ receptor or soluble analogues of the receptor. By way of example, phage libraries expressing random peptide sequences for selection on affinity columns comprising $Gb_3$ or after hybridisation with soluble radioactive $Gb_3$ analogues can be used. The glycolopid $Gb_3$ has been identified as being the cellular receptor of the Shiga toxin (Lingwood (1993), Adv. Lipid Res., 25: 189-211). $Gb_3$ is expressed by cells which are sensitive to the toxin and internalisation of the toxin would be permitted by an interaction with Gb$_3$. The present inventors have demonstrated that in HeLa cells in which expression of the Gb$_3$ receptor has been inhibited (FIG. 1A), the internalised B fragment is not transported into the Golgi apparatus but is accumulated in vesicular structures in the cytoplasm, principally represented by lysosomes. In the control cells, the B fragment is transported to the Golgi apparatus (FIG. 1B).

Figure 2:
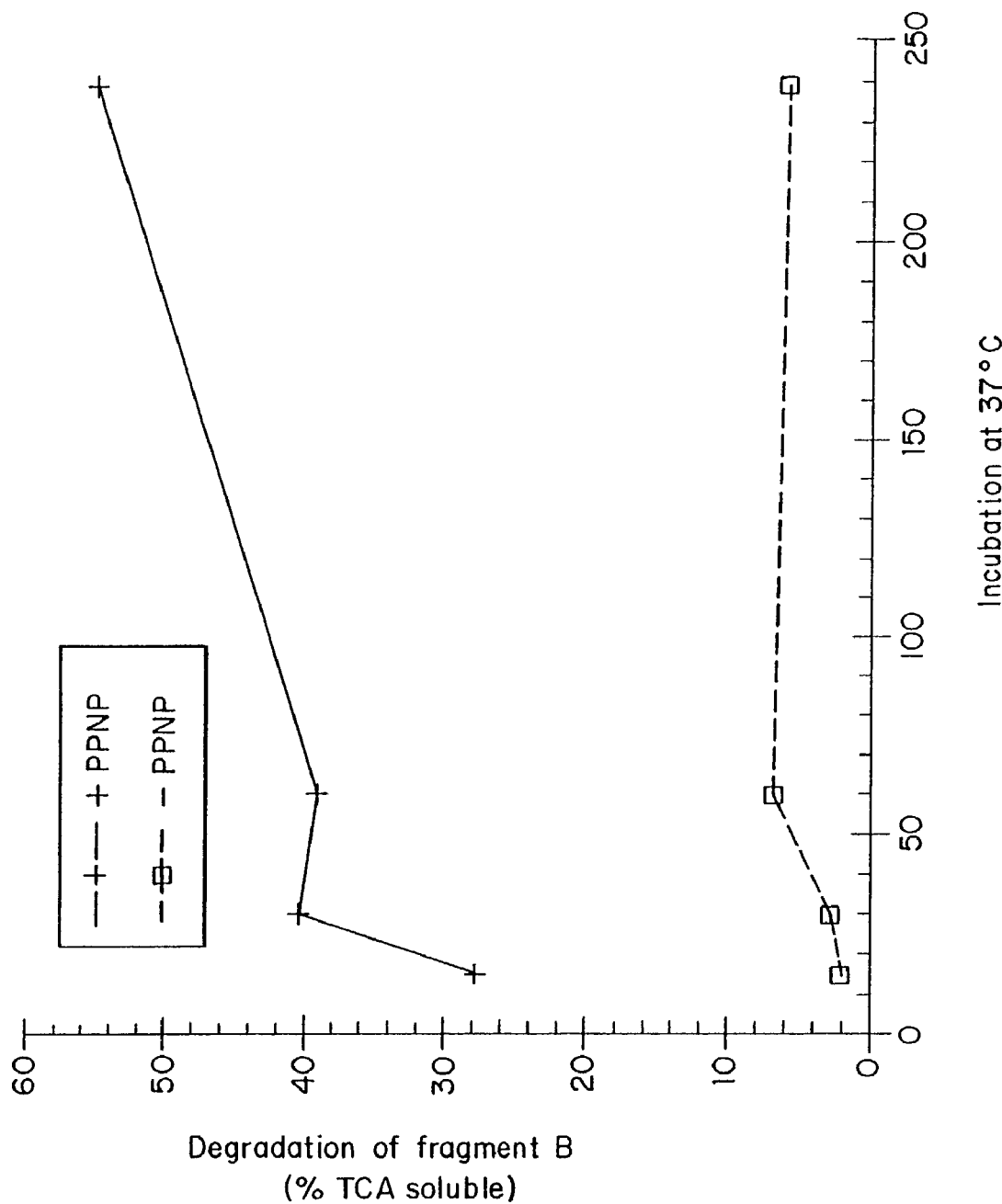

This hypothesis, whereby in the absence of the Gb$_3$ receptor, the B fragment is no longer transported to the biosynthesis system or secretion system, has been confirmed by biochemical experiments (FIG. 2).

The inventors have demonstrated that in the presence of an inhibitor of Gb$_3$ receptor synthesis, PPNP (+PPNP), up to 50% of the internalised B fragment is degraded in the form of TCA-soluble material, which conforms to a transport activity towards a subsequent degradation compartment such as an endosomal or lysosomal compartment. When Gb$_3$ receptor synthesis is not inhibited (−PPNP), a much smaller proportion of internalised B fragment becomes TCA soluble. It can thus be concluded that the presence of the Gb$_3$ receptor is necessary for addressing the B fragment to specific compartments, which tends to favour the fact the main factor in the activity of the B fragment is its binding to the Gb$_3$ receptor.

The present invention provides chimeric polypeptide sequences, said sequences comprising at least: the Shiga toxin B fragment or a functional equivalent thereof the carboxy-terminal end of which has bound to it one or more X polypeptides with the following formula:

B—X, wherein:

B represents the B fragment of a toxin such as the Shiga toxin, the sequence of which has been described by N. G. Seidah et al (1986), J. Biol. Chem. 261: 13928-31, and in Strockbine et al (1988), J. Bact. 170: 1116-22, or a functional equivalent thereof, or from verotoxin or from ricin (references supra);

X represents one or more polypeptides the upper limit to the total length of which being that of compatibility with retrograde or intracellular transport.

The present invention also provides chimeric molecules with the following structure:

B—X' where B has the same meaning as above and X' represents a nucleotide sequence coding for a peptide sequence X the expression of which is desired, in particular an antigen epitope.

The chimeric molecules of the invention can also comprise:
a) modification sites such as an N-glycosylation site constituted by about 20 amino acids, phosphorylation sites or any sequence necessary for any maturation of the molecule;
b) a retention signal of the tetrapeptide KDEL type (Lys-Asp-Glu-Leu) which, when it is bound to the carboxy-terminal end of resident ER proteins, causes retention after maturation of the proteins by passage into the Golgi apparatus. A discourse on the role of the retention signal in protein maturation has been provided by M. J. Lewis et al, (1992), cell, 68: 353-64.

More generally, the chimeric polypeptide sequences can comprise:
any sequence necessary for maturation of the protein in a suitable cellular system;
any sequence necessary for recognition of a given cell type by the chimeric molecule, thus enabling selectivity of action and penetration into the cell cytoplasm.

The common factor between all chimeric sequences with structure B—X or B—X' is that they contain the B fragment or a functional equivalent thereof.

The chimeric molecules of the invention enable X sequences or the expression product of X' to be routed in the ER. When X is bound to the B fragment, retrograde transport also occurs via the Golgi apparatus and probably via the endosomes. Further, under certain conditions, the molecules of the invention can undergo maturation leading to a membrane presentation of certain epitopes contained in the chimeric polypeptide sequence.

The term "maturation" means any process which, from a given polypeptide, leads to the emergence of peptides which themselves can be presented in a cellular compartment including the cytoplasm. Maturation can occur either by enzymatic clipping in the endoplasmic reticulum, or by transport into the cytoplasm in which the polypeptide is cleaved then the peptides obtained are again transported in the endoplasmic reticulum.

Molecules of the class I major histocompatibility complex (cl I MHC) can become charged with polypeptide molecules of interest X or X' after such cleavage and be presented on the cellular membranes.

When the chimeric molecule of the invention consists of coupling a B fragment or its equivalent with a polynucleotide molecule or an expression vector comprising a sequence the expression of which is desired, after transcription in the nucleus then translation in the cytoplasm, the polypeptide which is synthesised can undergo the same steps of cleavage, maturation and intracellular transport as that described above for a polypeptide chimeric sequence.

Chimeric polypeptide molecules in accordance with the invention can constitute an active principle in a therapeutic composition for immunotherapy by a mechanism which is close to biological processes regarding antigen presentation suitable for development of the immune reaction. The X fragment thus represents one or more epitopes for which membrane presentation is desired at the cell surface. The size of the X fragment is limited only by the intracellular transit capacity of the chimeric molecules under consideration.

This approach can be envisaged both for an anti-infectious or an anti-cancer immunotherapy and for constituting an antigenic bait in certain autoimmune diseases.

Any type of antigen presented by cl I MHC is a good candidate for selecting simple or chimeric epitopes which form part of the constructions of the invention. Examples which can be cited are:
a) Human Epitopes Derived from Melanoma Cell Proteins:
BAGE from tyrosinase (Boel, P et al (1995), Immunite 2, 167-75);
GAGE from gp75 (Van den Eynde, B. et al (1995), J. Exp. Med. 182, 689-98;
tyrosinase (Brichard V. et al (1993), J. Exp. Med. 178, 489-95);
p15 from A/MART-1 melanoma (Coulie P. G. et al (1994), J. Exp. Med. 180, 35-42; Kawakami Y. et al(1994), J. Exp. Med. 180, 347-52);
MAGE-1 and -3 from β-catenin (De Plaen E. et al (1994), Immunogenetics 40, 369-9; Traversari C et al (1992), J. Exp. Med. 176, 1453-7.
b) Human Epitopes Derived from Proteins Involved in Cancer Development:
Peptides derived from E6 and E7 proteins of HPV 16 (Feltkamp M. C. et al (1993), Eur. J. Immunol. 23, 2242-9; Davis H. L. et al (1995), Hum. Gene Ther. 6, 1447-56);

Peptides derived from the Hbs protein of HBV (Rehermann B. et al (1995), J. Exp. Med. 181 1047-58);

Peptides derived from proteins from EBV (Murray R. J. et al (1992), J. Exp. Med. 176, 157-68);

Peptide derived from cytomegalovirus.

c) Human Epitopes Derived from Oncogenes:

p21ras (Peace D. J. (1993), J. Immunother 14, 110-4; Ciernik, I. F. et al (1995) Hybridoma 14 139-42);

p53 (Gnjatic S. (1995), Eur. J. Immunol. 25, 1638-42).

d) Epitopes of Interest in Autoimmune Diseases:

These epitopes can be selected from those described by Chiez, R. M. et al (1994) in Immunol. Today 15, 155-60.

e) Epitopes of Interest in Infectious Diseases:

Examples of such epitopes which can be cited are those described by Furukawa K. et al (1994) in J. Clin. Invest. 94, 1830-9.

In the constructions of the invention, X or the expression product of X' can also represent a polypeptide sequence which can restore an intracellular transport function which has been perturbed by whatever cause. As an example, a biological molecule can be trapped in the ER due to a modification by mutation, deletion or addition of a sequence, having the effect of blocking maturation or transit of that molecule. This is the case, for example, with mutated CFTR ($\Delta$ F508) where binding to a chaperone molecule such as calnexin is modified such that its release is prevented or retarded, thus preventing intracellular transit. This mutation is the cause of cystic fibrosis. Introducing a non mutated replica into the endoplasmic reticulum could displace N glycosylated chains of the CFTR ($\Delta$ F508) glycoprotein from the interaction site with calnexin, with the result that protein transport to the plasma membrane is renewed, and the epithelial cells of the lung function normally.

The invention also provides nucleic acid constructions, in particular DNA or cDNA comprising a sequence of nucleotides coding for the chimeric protein the structure and variations of which have been defined above. More particularly, the invention provides expression vectors or plasmids carrying the above constructions and capable of being expressed in bacterial cultures. By way of example, the expression vector can be the pSU108 plasmid described by G. F. Su et al (1992), Infect. Immun. 60: 3345-59.

More particularly, the invention provides constructions comprising:

the sequence coding for the B fragment;

a sequence coding for one or more polypeptides the expression of which is desired. These may be epitopes the membrane expression of which is desired at the cell surface; they may also be polypeptides which can retain proteins in the Golgi apparatus; finally, they may be polypeptides which can restore a disturbed intracellular transport function.

The construction can also comprise any nucleic acid sequence coding for a polypeptide the presence of which enables proper intracellular transport in cells intended to be treated by the molecules of the invention. In particular, it may be:

a sequence coding for an N-glycosylation signal;

a sequence coding for the KDEL retention signal.

The polynucleotide construction of the invention is under the control of a promoter, preferably a strong promoter which can produce the correct degree of expression in bacteria into which it has been transfected.

The invention also provides transfected bacteria comprising these constructions, and capable of producing the chimeric polypeptides or proteins of the invention.

The host cells treated by the molecules of the invention also form part of the invention; they may be any type of cell, in particular:

those which can be treated in vivo such as immune system cells which are active in triggering cellular immunity, such as dendritic cells, macrophages or B lymphocytes;

those which can be treated in situ such as epithelial cells for use in restoring functions which have been altered either by a genetic defect or by a metabolic perturbation;

cancer cells.

In general, the chimeric molecules of the invention allow a novel therapeutic method to be postulated which can overcome the problems linked to viral vectors or retroviral vectors which are normally used to integrate and express exogenous molecules in animal cells. The therapeutic method which derives from the molecules of the invention consists of directly treating the cells of a patient, either ex vivo or by direct stereotaxic application with the chimeric polypeptide sequences, or by conventional mucosal treatment methods such as aerosols.

The invention concerns the use of chimeric polypeptide or polynucleotide sequences coding for the polypeptides of the invention in the production of therapeutic compositions in which particular polypeptides are expressed in the membranes of target cells. These polypeptides are advantageously epitopes against which the development of an immunological reaction is desired which are then presented on the surface of the immune system cells, in particular dendritic cells, macrophages or B lymphocytes. The B fragment of the Shiga toxin acts as an epitope vector enabling cells presenting, antigens to be programmed.

The present invention concerns an immunotherapeutic method consisting of increasing cellular immunity as the result of the presence of an undesirable antigen in an organism, said method consisting of causing key cells of the immune system, such as dendritic cells and macrophages, to express particular epitopes. The treatment method of the invention is aimed at triggering immunity to cellular and humoral mediation by charging the c1 I or c1 II MHC molecules with the epitopes of interest, after restriction in the target cells. This leads to activation of cytotoxic T cells against the antigen which it is desired to eliminate.

The epitopes presented through the constructions of the invention originate from viral, parasitic or bacterial antigens or from any cell, organite, or micro-organism the elimination of which is desired, such as cancer cells or infected cells. The epitopes can also act as bait enabling "self" molecules recognised as foreign antigens in autoimmune diseases to be replaced by the epitopes of the invention, thus slowing down or reducing the immune reaction.

Examples of these epitopes have been cited above in the description of the chimeric polypeptide sequences.

The invention also concerns the use of the chimeric molecules of the invention in the manufacture of therapeutic compositions in which the particular polypeptides which it is desired to express can restore intracellular transit of a protein the altered structure of which leads to it being trapped in the ER and to an expression deficit. This is the case for membrane expression proteins which undergo intracellular maturation, including glycosylations, sulphatations, folding etc.

A particular example is that of mutated CFTR (Δ F508) wherein the attachment of a chaperone molecule such as calnexin is modified following modification of the protein; this leads to the molecule being trapped, causing cystic fibrosis, leading to a general insufficiency of exocrin secretions, in particular in the pancreas and lungs.

The present invention concerns a therapeutic treatment method for diseasep having an origin in a fault in protein secretion; the method consists of directly administering the chimeric polypeptides or administering the genetic information to the cells of patients in the form of plasmids trying exogenic sequences coding for a peptide or polypeptide which can restore the deficient cellular function.

This restoration can result either in supplementation of the deficient function by the polypeptide X or competition between the mutated protein and the polypeptide synthesised from the exogenic sequence for binding with a specific molecule or receptor of the cellular machinery. A particular example is the treatment of the mutant cited above, causing cystic fibrosis, by administering a vector carrying a sequence coding for the attachment site for the CFTR protein with its chaperone molecule or by direct administration of the chimeric polypeptide.

The constructions of the invention endow the human or animal health world with a novel therapeutic means for treating diseases caused by a deficit in intracellular transit or for increasing or inducing a membrane presentation of a molecule, a polypeptide or an epitope of interest.

Further properties of the invention will become clear from the following examples and figures.

KEY TO FIGURES

FIG. 1)A: HeLa cells in which expression of the $Gb_3$ receptor has been inhibited. The internalised B fragment is not transported to the Golgi apparatus but is accumulated in the vesicular structures.

FIG. 1)B: Control HeLa cells in which the B fragment is transported to the Golgi apparatus.

FIG. 2: Biochemical test showing the defect in B fragment transport.

Figure 3:
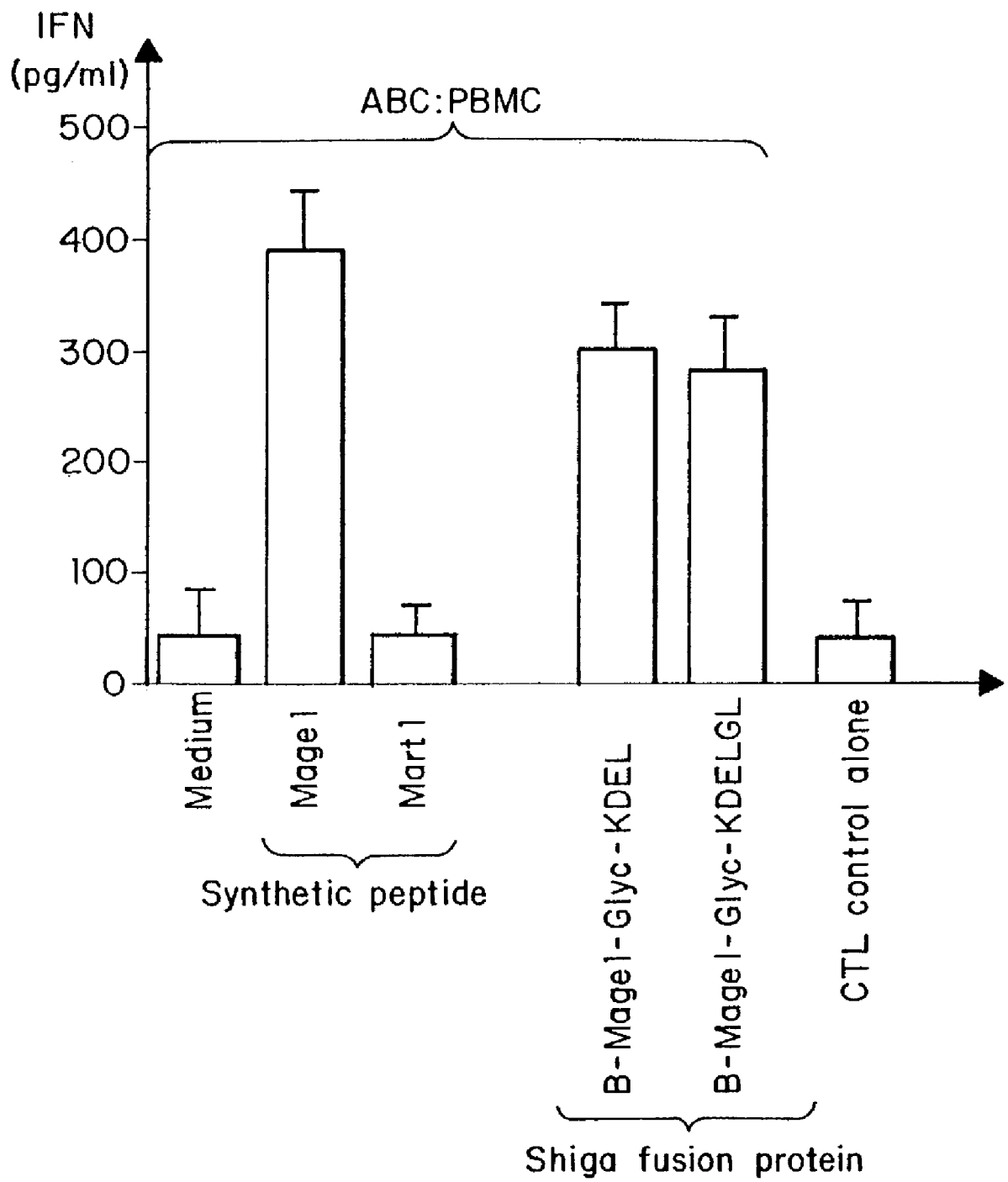

FIG. 3: MHC class I restricted presentation of Shiga B-Mage 1 fusion proteins at peripheral blood monocytic cells (PBMC): role of the KDEL sequence. The PBMC ($5 \times 10^4$) were primed overnight with either Mage 1 peptide (1 µM) or Mart 1 peptide (1 µM) or Shiga B-Mage 1 fusion proteins (1 µM) with a sequence which is active (B-Mage 1-Glyc-KDEL) or inactive (B-Mage 1-Glyc-KDELGL) for recycling to the endoplasmic reticulum. After washing, $2 \times 10^4$ cytotoxic T cells specific for the Mage 1 epitope (clone 82/30) were incubated with PBMC cells primed for 24 hours. The supernatants were then collected and tested for the production of γ interferon.

Figure 4:
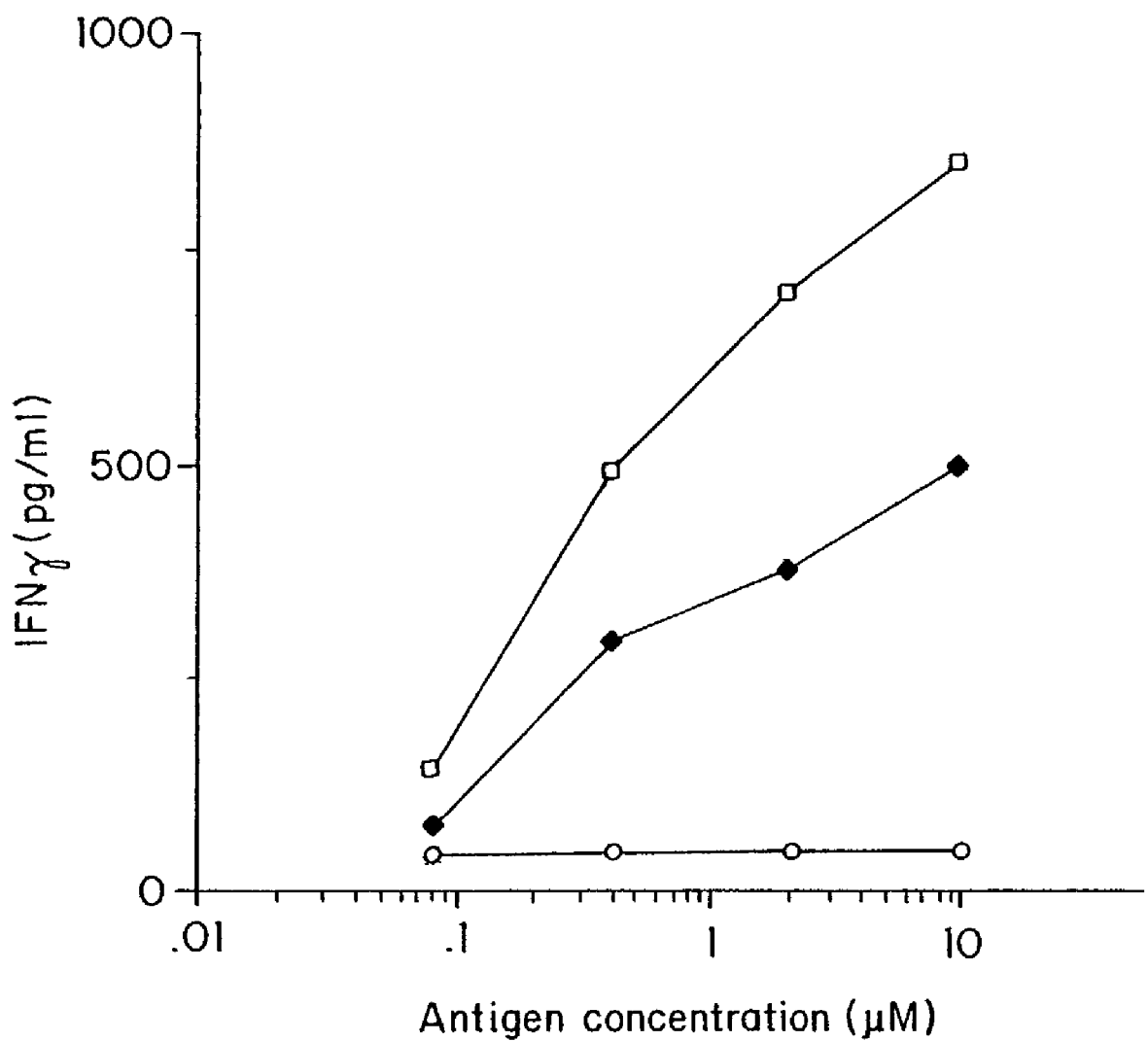

FIG. 4: MHC class I restricted presentation of the Shiga B-Mage 1 fusion protein by different types of cells presenting antigens. B lymphoblastoid-cells (▱), dendritic cells (+) or clonal T cells (▨) were primed with the soluble Shiga B-Mage 1 fusion protein, as for FIG. 3. Presentation of Mage 1 peptides was tested using the 82/30 CTL line.

Figure 5:
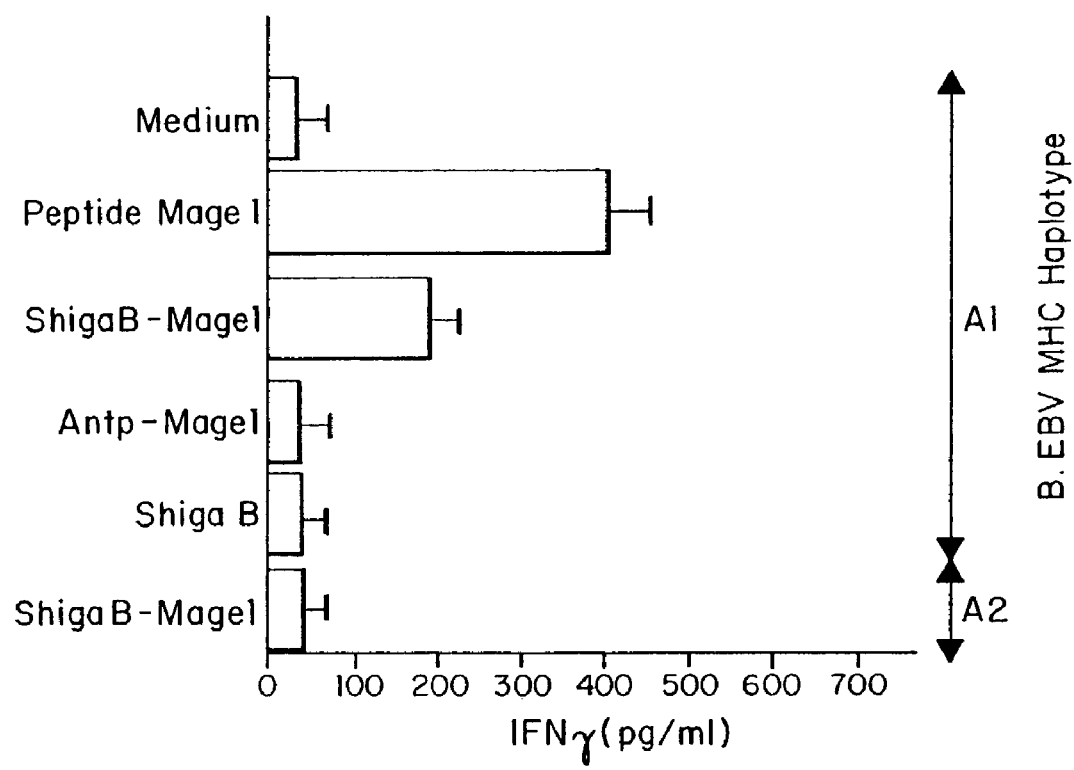
Figure 5:
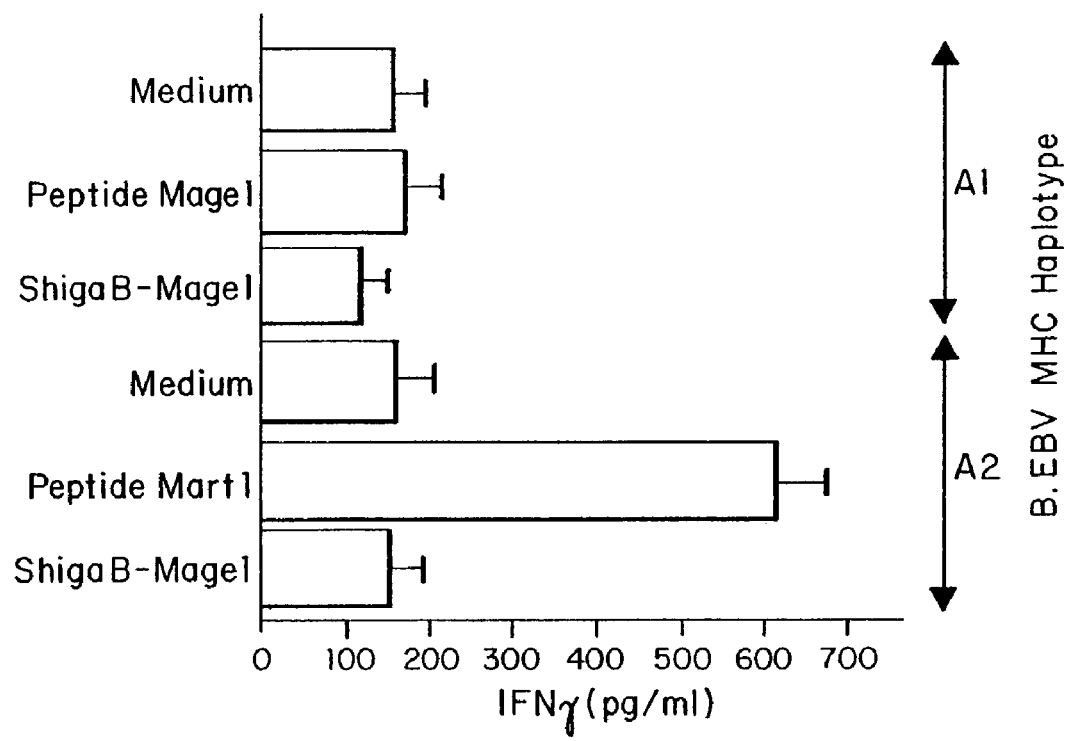

FIG. 5: Analysis of the specificity of the MHC class I restricted presentation of the Shiga B-Mage 1 fusion protein by lines of B lymphoblastoid cells. Cells from the BM21 (HLA-A1) or BV1 (HLA-A2) B lymphoblastoid line were primed overnight either with medium alone or with Mage 1 or Mart 1 synthetic peptides (1 µM), or with ShigaB-Mage 1 fusion protein (1 µM), or with Antp-Mage 1 fusion protein or with the B fragment of wild-type Shiga toxin. After washing, specific cells of Mage 1 TCL 82/30 (A) or Mart 1 CTL LB373 (B) were incubated for 24 hours with primed B-EBV cells. The supernatants were then collected and tested for the production of γ interferon.

I—CONSTRUCTION OF A RECOMBINANT CHIMERIC POLYNUCLEITIDE AND THE PRODUCTION OF THE CORRESPONDING POLYPEPTIDE

I-1) Construction of Plasmid

The X epitope selected was the MAGE epitope, present in cancer cells of patients with melanoma. The plasmid used was the pSU108 plasmid described by Su et al, 1992, Infect. Immun. 60: 33-45, 3359.

The PCR primers used were as follows:

```
SEQ ID No. 1:
5'-ACTAGCTCTGAAAAGGATGAACTTTGAGAATTCTGACTCAGAATAGC
                                                  TC-3'
SEQ ID No. 2:
5'-CTTTTCAGAGCTAGTAGAATTAGGATGATAGCGGCCGCTACGAAAAA
                                           TAACTTCGC-3'
```

The primers were used with specific primers from the ShigaAtpE (5') vector

```
SEQ ID No. 3: 5'-CACTACTACGTTTTAAC-3'

SEQ ID No. 4: 5'-CGGCGCAACTATCGG-3'
``` to produce fragments which were cloned at the restriction sites SphI and SalI of the SU108 plasmid.

Adapter fragments containing the glycosylation site and the KDEL sequence composed of the oligonucleotides sulphate 1: ((5'-phosphorylated; 5'-GGCCGCCATCCTAATTC-TACTTCT-3' (SEQ ID No. 5)) and sulphate 2 (5'-CTCA-GAAGTAGAATTAGGATGGC-3' (SEQ ID No. 6)) or sulphate 3 (5'-GAGTCTGAAAAAGATGAACTTTGAT-GAG-3' (SEQ ID No. 7)) were ligatured overnight at 16° C.

The resulting fragments were cloned at the NotI and EcoRI restriction sites of pSU108 and containing the cDNA coding for B-Glyc-KDEL.

I-2) Purification of Proteins

The recombinant fragments were also purified using the technique described by Su et al, 1991, cited above. In brief, *E. coli* cells containing recombinant expression plasmids obtained from pSU108 were cultured overnight at 30° C. The culture was then diluted 5 times in LB supplemented with 50 mg/ml of ampicillin, at 50° C. After incubation for 4 hours at 42° C., the cells were thoroughly washed with 10 mM Tris/HCL, pH 8, incubated for 10 minutes in 10 mM Tris/Hcl, pH 8; 25% sucrose, 1 mM EDTA, and finally rapidly re-suspended in a water-ice mixture containing 1 mM of PMSF and a protease inhibitor mixture (leupeptin, chymostatin, pepstatin, antipain and aprotinin). The final step led to rupture of the periplasm. After clarification, the supernatant was charged onto a QFF column (Pharmnacia) and eluted with a linear gradient of NaCl in 20 mM Tris/HCl, pH 7.5. depending on the construction, the B fragment was eluted between 120 mM and 400 mM. The fractions containing the B fragment were then dialysed against 20 mM of Tris/HCl, pH 7.5, and re-charged onto a monoQ column (Pharmacia) and eluted in the same manner as before. The resulting proteins, estimated to have a degree of purity of 95% using polyacrylamide-SDS gel electrophoresis, were then stored at −80° C. until use.

I-3) Induction of a CTL Response In Vitro

Dendritic cells (DC) were cultured using previously established protocols (Romani et al, 1994). Briefly, PBMC were taken up into suspension in Iscove medium and incubated for 2 h at 37° C. in 6-well trays. Cells which had not adhered were removed and the remaining cells were incubated at 37° C. in the presence of GM-CSF (800 U/ml) and IL-4 (500 U/ml). After 5 days culture, the IL-1α and IFN-γ in respective concentrations of 50 U/ml and 150 U/ml were added and incubation was continued at 30° C. for 24 h. The dendritic cells were then taken up into suspension in Iscove medium in the presence of increasing concentrations of B fragment coupled with the MAGE epitope and in the presence of 3 µg/ml of human β2-microglobulin to improve the capacity of the cells to presentation of membrane epitopes. This mixture was incubated at 30° C. for 4 hrs. DCs which had internalised the B fragment coupled to this epitope were irradiated at 5000 rad, assembled by centrifuging, taken up into suspension, and mixed with CD8+ lymphocytes (prepared from PBMC). These DC, pulsed with an antigen, and the CD8+ were then kept in co-culture in the presence of 5 ng/ml of IL-7.

After 10 days, responsive CD8+ lymphocytes were re-stimulated by freshly prepared irradiated DCs which were then also incubated in the presence of increasing concentrations of fragment B coupled to the same epitope. The co-culture of DC and responsive CD8+ lymphocytes was continued in the presence of IL-2 and IL-7 in concentrations of 10 U/ml and 5 ng/ml respectively. This re-stimulation protocol was repeated 3 times.

In order to measure the introduction of a CTL response, responsive CD8+ lymphocytes pre-stimulated as described above were incubated in the presence of cancer cells or cells infected with a virus. These cells, which expressed the selected epitope, were labelled with $Na_2^{51}CrO_4$ then brought into contact with responsive CD8+ for 5 hours (Bakker et al, 1994). The radioactivity released in the medium was then determined, enabling the cytotoxic activity of the pre-stimulated responsive CD8+ lymphocytes to be quantified.

Results

II—Presentation of the Mage 1 Antigen by Pena-EBV Cells and Dendritic Cells Pulsed by a B Fragment of the Shiga Toxin Carrying this Antigen II-1) Morphological Study of Intracellular Transport of a B Fragment Carrying the MAGE-1 Epitope We have demonstrated that it is possible to fuse a peptide sequence to the carboy-terminal end of the Shiga toxin B fragment while retaining intracellular routing of this protein towards the endoplasmic reticulum (ER). This demonstration was carried out by constructing chimeric polypeptides comprising the B fragment, the N-glycosylation site and the KDEL retention signal. As a control, the KDELGL retention signal was used, namely the inactive version of the KDEL peptide, Misendock and Rothman, 1995, J. Cell. Biol. 129: 309-319. Morphological and biochemical studies have shown that the modified B fragment is transported from the plasmid membrane via the endosomes and the Golgi apparatus to the endoplasmic reticulum. This transport is inhibited by BFA (brefeldin A fungal metabolite) and reduced by nocodazole (a microtubule depolymerisation agent).

These experiments clearly demonstrate that intracellular routing of the fusion protein towards the endoplasmic reticulum was retained. To evaluate the potential of the B fragment as an epitope vector for anti-tumoral vaccination in vitro, the MAGE-1 epitope was added to the B-Glyc-KDEL fragment under the etperimental conditions described above. The novel protein was designated B-MAGE-Glyc-KDEL. The B-MAGE-Glyc-KDEL protein was coupled with the fluorophore DTAF in order to follow its intracellular transport by confocal microscopy. After internalistion, this protein was detectable in the Golgi apparatus and in the ER of HeLa cells and Pena-EBV cells (a B lymphocyte line inmmortalised using the Epstein-Barr virus). These results confirm the original observations concerning the intracellular transport of the B fragment modified at its carboxy-terminal end (described above) and affirm that certain presenting cells of the hematopoietic line are capable of internalising the B fragment and transporting the protein to the ER.

We shall now describe these studies measuring the N-glycosylation of the B-MAGE-Glyc-KDEL protein. N-glycosylation is a modification which is carried out specifically in the ER, and we have demonstrated above that a B fragment carrying a recognition site for N-glycosylation is in fact glycosylated if it is transported to the ER.

II-2) Study of the Presentation of the MAGE-1 Antigen by Pena-EBV Cells and Dendritic Cells Pulsed by the B-MAGE-Glyc-KDEL Protein In order to evaluate the capacity of the fragment to act as an epitope vector, we used a cytotoxic T lymphocyte clone (CTL 82/30) specifically recognising the MAGE-1 epitope associated with MHC class I of cells presenting the HLA-A1 haplotype. These CTL were kept in the presence of Pena-EBV cells or dendritic cells pulsed with the B-MAGE-Glyc-KDEL protein. If the MAGE-1 epitope is presented by presenting cells, the CTL will be activated and will secrete γ interferon which (IFNγ) which is then assayed.

The quantity of IFNγ secreted is proportional to the amplitude of the stimulation of the CTLs by the presenting cells.

Presenting cells (Pena-EBV and dendritic, 20000 cells per round bottom microwell) were either fixed for 1 h with 4% PBS-paraformaldehyde, or were not fixed. They were than washed twice with OptiMEM before being incubated for 15 h with dilutions of the B-MAGE-Glyc-KDEL protein. The protein was tested at 4 dilutions, starting with a concentration of 10 µmM final, and diluting 5 in 5 in the OptiMEM medium (medium without serum). After 15 h, the plates were washed twice by low speed centrifuging. The CTL (CTL 82/30) were added in an amount of 5000 CTL per well in 100 µl of culture medium (ID-HS-AAG+25 U/ml of IL2). As a positive control, some CTL 82/30 were kept in the presence of line G43 (a B lymphocyte line transfected with an expression plasmid of MAGE-1). After 24 h of incubation, the supernatants were harvested to determine the quantity of IFNγ produced.

The results are shown in Table I.

TABLE I

| Cell type | | Concentration of B-MAGE-Glyc-KDEL | | | |
|---|---|---|---|---|---|
| | | 10 µM | 2 µM | 0.4 µM | 0.08 µM |
| Dendritic | Fixed | 446 ± 293 | 821 ± 64 | 661 ± 18 | 312 ± 181 |
| | Non fixed | 1557 ± 404 | 1315 ± 91 | 1231 ± 150 | 1174 ± 478 |
| Pena-EBV | Fixed | 70 ± 47 | 68 ± 48 | 23 ± 32 | 4 ± 5 |
| | Non fixed | 1966 ± 415 | 1960 ± 206 | 1544 ± 42 | 853 ± 116 |

The results are represented by the amount of IFNγ produced under each set of conditions (average±standard deviation; n=3).

We can see that the dendritic cells and the Pena-EBV cells pulsed with the B-MAGE-Glyc-KDEL protein were properly recognised by the CTL, even at low concentrations of the protein. In contrast, the dendritic cells and the Pena-EBV cells which had been previously fixed were not recognised. It thus appears that endocytosis and processing of the B-MAGE-Glyc-KDEL protein had taken place. These encouraging results will now be backed up by in vitro vaccination experiments.

III—In Vivo Anti-tumoral and/or Antiviral Activity Test in the Mouse

Mouse dendritic cells were prepared and marked with an antigen derived from P21RAS, P53 or EP2/NER proteins to test the anti-tumoral activity, or HBV, EBV or BPV to test antiviral activity. This preparation of dendritic cells was carried out using the protocol described in I-4) above.

These dendritic cells were then introduced into the mouse.

The antiviral or anti-tumoral effect was observed by subsequent treatment of these mice grafted with tumoral cells or virus expressing this antigen.

Conclusion

The polypeptide-sequences or polynucleotide sequences of the invention can thus advantageously constitute an active principle in a pharmaceutical composition intended for the treatment of certain cancers or certain viral or bacterial infections, from the moment when a particular epitope of said virus or said cancer cell will have been integrated into the recombinant nucleotide sequence, leading to synthesis of a chimeric polypeptide which can be restricted by the MHC class I and can be expressed on the membrane surface of immune system cells.

IV—Restoration of Intracellular Transport of the Mutated Protein CFTR (ΔF508) Using the Shiga Toxin B Fragment The CFTR (cystic fibrosis transmembrane regulator) protein is a chlorine channel of the plasmic membrane. In the large majority of patients with cystic fibrosis, the CFTR gene carries mutations. The mutation (ΔF508) which is the most frequently observed affects intracellular routing of the CFTR protein. In fact, the mutated protein CFTR(ΔF508), which is functional as regards its ionic channel activity, remains blocked at the endoplasmic reticulum, instead of being transported to the plasmic membrane. Using the Shiga toxin B fragment, we have introduced a domain of the CFTR protein which is known to be the domain of interaction with the calnexin protein (ER "chaperone") into the endoplasmic reticulum. This domain is fused to the carboxy-terminal end of the B fragment. We have tested whether this chimeric protein can displace N-glycosylated chains of the CFTR (ΔF508) glycoprotein from the interaction site with calnexin, with the result that the CFTR(ΔF508) protein is no longer retained in the endoplasmic reticulum and can be transported to the plasmic membrane and thus function normally.

Firstly, we constructed a chimeric protein composed of a B fragment and the interaction domain-derived from the CFTR protein. A recycle signal (the KDEL peptide) was added to the carboxy-terminal end of this protein to increase its retention in the endoplasmic reticulum. It was first verified that the novel protein was also transported in the endoplasmic reticulum of target cells. Mobilisation of CFTR(ΔF508) was studied in cells of a stable cell line, LLCPK1, tansfected within the CDNA of CFTR(ΔF508). This line was established by Mile. M. A. Costa de Beauregard and M. D. Louvard (Institut Curie, Paris, CNRS ULMR 144). The CFTR (ΔF508) protein which was expressed in these cells was also endowed with an epitope tag. It was thus possible to detect the arrival of the CFTR (ΔF508) protein in the plasmic membrane by immunofluorescence. In the absence of treatment, the plasmic membrane of LLCPK1 cells of the line was depleted with specific CFTR (ΔF508) tags in the plasmic membrane. While the results of these pilot experiments are promising, we are obliged to develop this approach within the context of cystic fibrosis therapy.

Conclusion

The experiment described above shows that the synthetic polypeptide in which X is constituted by an interaction domain between the CFTR protein and calnexin can advantageously constitute the active principle of a therapeutic composition intended to treat cystic fibrosis. In fact, competition between the mutated interaction domain in the mutant and the fragment of synthetic polypeptide for the interaction with calnexin can restore secretion of the mutated protein in the bronchia.

Antigenic presentation test:

Cells presenting the antigen (CMSP, B-EBV cells, T cells, dendritic cells) were incubated in 96-well microplates in a density of $10^5$ cells per well and pulsed at 37° C. for 4 hours or 15 hours with the antigen dissolved in 100 μl of Iscove medium. After incubation, the medium was removed and 20000 CTL cells were added to each well in 100 μl of CTL culture medium containing 25 U/ml of IL2. After 24 hours, 50 μl of supernatant was collected and the γ interferon was measured by an ELISA (Diaclone) test. In some experiments, the cells were fixed with 1% paraformaldehyde for 10 minutes at ambient temperature and washed thoroughly before transfer into the microplates.

The invention claimed is:

1. A chimeric molecule comprising a Shiga toxin B fragment bound to one or more polynucleotides, X', wherein X' is a polynucleotide sequence coding for a polypeptide, X.

2. The chimeric molecule of claim 1, wherein X is an epitope which can be presented by the class I major histocompatibility complex.

3. The chimeric molecule of claim 2, wherein X is an epitope of a polypeptide or a protein, wherein the expression of said polypeptide or protein is desired at the surface of cells of the immune system.

4. The chimeric molecule of claim 3, wherein said protein or polypeptide is a cancer cell protein, a virus protein or an oncoprotein.

5. The chimeric molecule of claim 4, wherein X is a MAGE epitope derived from melanoma cells.

6. A composition, comprising the chimeric molecule of claim 1.

7. The composition of claim 6, wherein said composition restores deficits in intracellular transport.

8. The composition of claim 6, wherein said composition stimulates the immune defenses of the organism towards viral, parasitic or bacterial infections or cancerous antigens.

* * * * *

UNITED STATES PATENT AND TRADEMARK OFFICE
CERTIFICATE OF CORRECTION

PATENT NO. : 7,488,809 B2  Page 1 of 1
APPLICATION NO. : 10/443614
DATED : February 10, 2009
INVENTOR(S) : Bruno Goud It is certified that error appears in the above-identified patent and that said Letters Patent is hereby corrected as shown below:

On the Title Page, item (73) should read:
(73) ~~Insem-Transfert~~ Inserm-Transfert, Paris (FR); Universite Pierre Et Marie Curie (UPMC), Paris (FR)

Signed and Sealed this

Twenty-first Day of April, 2009

JOHN DOLL
*Acting Director of the United States Patent and Trademark Office*

SEQUENCE LISTING

<160> NUMBER OF SEQ ID NOS: 10

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 1
actagctctg aaaaggatga actttgagaa ttctgactca gaatagctc         49

<210> SEQ ID NO 2
<211> LENGTH: 56

```
<212> TYPE: DNA
<213> ORGANISM: Artificial Sequence
<220> FEATURE:
<223> OTHER INFORMATION: Description of Artificial Sequence: Primer

<400> SEQUENCE: 2
cttttcagag ctagtagaat taggatgata gcggccgcta cgaaaaataa cttcgc          56

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
cactactacg tttttaac                                                    17

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 4
cggcgcaact atcgg                                                       15

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ggccgccatc ctaattctac ttct                                             24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
ctcagaagta gaattaggat ggc                                              23

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 7
gagtctgaaa aagatgaact ttgatgag                                         28

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Polypeptide

<400> SEQUENCE: 8
```

```
Lys Asp Glu Leu
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Polypeptide

<400> SEQUENCE: 9

His Asp Glu Leu
  1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Polypeptide

<400> SEQUENCE: 10

Lys Asp Glu Leu Asp Leu
  1               5
```